United States Patent
Noy

(10) Patent No.: US 7,759,069 B1
(45) Date of Patent: Jul. 20, 2010

(54) COMPOSITIONS AND METHODS FOR MEASURING NUCLEAR RECEPTOR LIGANDS

(75) Inventor: Noa Noy, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 11/294,736

(22) Filed: Dec. 6, 2005

Related U.S. Application Data

(60) Provisional application No. 60/634,764, filed on Dec. 9, 2004.

(51) Int. Cl.
*G01N 33/53* (2006.01)

(52) U.S. Cl. .................. 435/7.1; 435/7.2; 435/7.21; 436/86; 436/501

(58) Field of Classification Search .................. None
See application file for complete search history.

(56) References Cited

OTHER PUBLICATIONS

Fruchart et al. (Current Opinion in Lipidology, 1999, vol. 10, pp. 245-257).*
Tian et al. (Biochemistry, vol. 36, 1997, pp. 5669-5676).*
Fischer et al. (The Journal of Biological Chemistry, vol. 278,No. 30 Jul. 25, 2003, pp. 27997-28004).*
Staels et al. (Biochimie, 1997, vol. 79, pp. 95-99).*
Fruchart et al. (Current Opinion in Lipidology, 1999, vol. 10, pp. 245-257), Some.*
Norris et al. (Biochimica et Biophysica Acta, vol. 1209, 1994, pp. 10-18).*
Stefanova et al. (Biochemistry, 1993, vol. 32, pp. 6095-6103).*
Pastukhov et al. (Proteins:Structure, Function, and Genetics, vol. 53, 2003, pp. 607-615).*
Li et al. (The Journal of Biological Chemistry, vol. 265, No. 20, Issue of Jul. 15, 1990, pp. 11549-11554).*
Ignatova et al. (Proceeding of the National Academy of Sciences, Jan. 13, 2004, vol. 101, No. 2, pp. 523-528).*
Formelli, F. Correspondence Re: Lanvers C. et al. "Pharmacology of All-Trans-Retinoic Acid in Children With Acute Promyelocytic Leukemia. Med Pediatr Oncol 2003; 40:293-301" *Pediatr Blood Cancer* 42:392-3 (2004).
Hamada, K. et al. "H-2RIIBP, a Member of the Nuclear Hormone Receptor Superfamily that Binds to Both the Regulatory Element of Major Histocompatibility Class I Genes and the Estrogen Response Element" *Proc. Natl. Acad. Sci. USA* 86:8289-93 (1989).
Kersten, S. et al. "Role of Ligand in Retinoid Signaling. 9-*cis*-Retinoic Acid Modulates the Oligomeric State of the Retinoid X Receptor" *Biochemistry* 34(42):13717-21 (1995).
Kersten, S. et al. "On the Role of Ligand in Retinoid Signaling: Positive Cooperativity in the Interactions of 9-*cis* Retinoic Acid with Tetramers of the Retinoid X Receptor" *Biochemistry* 34:14263-69 (1995).
Mangelsdorf, D.J., et al. "Characterization of Three RXR Genes that Mediate the Action of 9-*cis* Retinoic Acid" *Genes & Development* 6:329-44 (1992).
Mangelsdorf, D.J., et al. "Nuclear Receptor that Identifies a Novel Retinoic Acid Response Pathway" *Nature* 345:224-9 (1990).

* cited by examiner

*Primary Examiner*—Lisa V Cook
(74) *Attorney, Agent, or Firm*—Burns & Levinson, LLP; Jacob N. Erlich, Esq.; Janine M. Susan

(57) ABSTRACT

Disclosed herein are compositions and methods used for detecting and measuring ligands for nuclear receptors and intracellular lipid binding proteins in both in vitro and in vivo samples.

11 Claims, 7 Drawing Sheets

```
                 1                                      *          50
    CRABP-II  ...MPNFSGN WKIIRSENFE ELLKVLGVNV MCRKIAVAAA SKPAVEIKQE
     CRABP-I  ...MPNFAGT WKMRSSENFD ELLKALGVNA MCRKVAVAAA SKPHVEIRQD
        FABP  ..MVDAFLGT WKLVDSKNFD DYMKSLGVGF ACRQVASMT. .KPTTIIEKN
       brain  ..MVEAFCAT WKLTNSQNFD EYMKALGVGF ACRQVGNVT. .KPTVIISQE
   adipocyte  ..MCDAFVGT WKLVSSENFD DYMKEVGVGF ACRKVAGMA. .KPNMIISVN
        PMP2  ..MSNKFLGT WKLVSSENFD DYMKALGVGL ACRKLGNLA. .KPTVIISKK
 keratinocyte MATVQQLEGR WRLVDSKGFD EYMKELGVGI ACRKMGAMA. .KPDCIITCD
      CRBP-I  ..MPVDFTGY WKMLVNENFE EYLRALDVNV ACRKIANLL. .KPDKEIVQD
    CRBP-III  ..MPPNLTGY YRFVSQKNME DYLQALNISL ACRKIALLL. .KPDKEIEHQ
     CRBP-II  ..MTRDQNGT WEMESNENFE GYMKALDIDF ACPKIAVRL. .TQTKVIDQD
     CRBP-IV  ..MPADLSGT WTLLSSDNFE GYMLALGIDF ACRKIAKLL. .KPQKVIEQN
  intestinal  ....MAFDST WKVDRSENYD KFMEKMGVNI VCRKLAAHD. .NLKLTITQE
       liver  ....MSFSGK YQLQSQENFE AFMKAIGLPE ECIQKGKDI. .KGVSEIVQN
       ileal  ....MAFTGK FEMESEKNYD EFMKLLGISS DCIEKARNF. .KIVTEVQQD 51                                                100
    CRABP-II  GDTFYIKTS. TTVRTTEINF KVGEEFEE.. QTVDGRPCKS LVKWESENKM
     CRABP-I  GDQFYIKTS. TTVRTTEINF KVGEGFEE.. ETVDGRKCRS LATWENENKI
       heart  GDILTLKTH. STFKNTEISF KLGVEFDE.. TTADDRKVKS IVTLDGG.KL
       brain  GDKVVIRTL. STFKNTEISF QLGEEFDE.. TTADDRNCKS VVSLDGD.KL
   adipocyte  GDLVTIRSE. STFKNTEISF KLGVEFDE.. ITADDRKVKS IITLDGG.AL
        PMP2  GDIITIRTE. STFKNTEISF KLGQEFEE.. TTADNRKTKS IVTLQRG.SL
 keratinocyte GKNLTIKTE. STLKTTQFSC TLGEKFEE.. TTADGRKTQT VCNFTDG.AL
      CRBP-I  GDHMIIRTL. STFRNYIMDF QVGKEFEEDL TGIDDRKCMT TVSWDGD.KL
    CRBP-III  GNHMTVRTL. STFRNYTVQF DVGVEFEEDL RSVDGRKCQT IVTWEEE.HL
     CRBP-II  GDNFKTKTT. STFRNYDVDF TVGVEFDEYT KSLDNRHVKA LVTWEGD.VL
     CRBP-IV  GDSFTIHTN. SSLRNYFVKF KVGEEFDEDN RGLDNRKCKS LVIWDND.RL
  intestinal  GNKFTVKES. SAFRNIEVVF ELGVTFNY.. NLADGTELRG TWSLEGNKLI
       liver  GKHFKFTIT. AGSKVIQNEF TVGEECEL.. ETMTGEKVKT VVQLEGDNKL
       ileal  GQDFTWSQHY SGGHTMTNKF TVGKESNI.. QTMGGKTFKA TVQMEG.GKL 101                            145
    CRABP-II  VCEQKLLKGE GPKTSWTREL TNDGELILTM TADDVVCTRV YVRE.   (SEQ ID NO:2)
     CRABP-I  HCTQTLLEGD GPKTYWTREL AND.ELILTF GADDVVCTRI YVRE.   (SEQ ID NO:3)
       heart  VHLQ...KWD GQETTLVREL IDG.KLILTL THGTAVCTRT YEKEA   (SEQ ID NO:4)
       brain  VHIQ...KWD GKETNFVREI KDG.KMVMTL TFGDVVAVRH YEKA.   (SEQ ID NO:5)
   adipocyte  VQVQ...KWD GKSTTIKRKR DGD.KLVVEC VMKGVTSTRV YERA.   (SEQ ID NO:6)
        PMP2  NQVQ...RWD GKETTIKRKL VNG.KMVAEC KMKGVVCTRI YEKV.   (SEQ ID NO:7)
 keratinocyte VQHQ...EWD GKESTITRKL KDG.KLVVEC VMNNVTCTRI YEKVE   (SEQ ID NO:8)
      CRBP-I  QCVQ...KGE KEGRGWTQWI EGD.ELHLEM RVEGVVCKQV FKKVQ   (SEQ ID NO:9)
    CRBP-III  VCVQ...KGE VPNRGWRHWL EGE.MLYLEL TARDAVCEQV FRKVR   (SEQ ID NO:10)
     CRBP-II  VCVQ...KGE KENRGWKQWI EGD.KLYLEL TCGDQVCRQV FKKK.   (SEQ ID NO:11)
     CRBP-IV  TCIQ...KGE KKNRGWTHWI EGD.KLHLEM FCEGQVCKQT FQRA.   (SEQ ID NO:12)
  intestinal  GKFKR..TDN GNELNTVREI IGD.ELVQTY VYEGVEAKRI FKKD.   (SEQ ID NO:13)
       liver  VT.......T FKNIKSVTEL NGD.IITNTM TLGDIVFKRI SKRI.   (SEQ ID NO:14)
       ileal  VV.......N FPNYHQTSEI VGD.KLVEVS TIGGVTYERV SKRLA   (SEQ ID NO:15)
```

Figure 2B.

| Protein | Alternate names | Mutation | Sequence accession # |
|---|---|---|---|
| CRABP-II | | L29C | P29373 |
| CRABP-I | | L29C | P29762 |
| Heart FABP | Muscle-FABP, MDGI, FABP3 | T30C | P05413 |
| Brain FABP | BLBP, MDGI-related, FABP7 | T30C | O15540 |
| Adipocyte FABP | AP2, P15, ALBP, 422 protein, FABP4 | T30C | P04117 |
| PMP2 | peripheral myelin protein 2 | T30C | NP_002668 |
| Keratinocyte FABP | EFABP, PA-FABP, FABP5 | L32C | Q01469 |
| CRBP-I | | L30C | P09455 |
| CRBP-III | | V30C | P82980 |
| CRBP-II | HRBPiso | T30C | P50120 |
| CRBP-IV | Retinoid binding protein 7 | T30C | Q96R05 |
| Intestinal FABP | FABP2 | K28C | NP_000125 |
| Liver FABP | FABP1 | L28C | NP_001434 |
| Ileal LBP | ILBP, gastotropin, GT, I-BABP, I-15P, FABP6 | V28C | P51161 |

SEQUENCE LISTING

```
<160> NUMBER OF SEQ ID NOS: 15

<210> SEQ ID NO 1
<211> LENGTH: 71
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(38)
<223> OTHER INFORMATION: Xaa can be any naturally occurring amino acid
<220> FEATURE:
<221> NAME/KEY: misc_feature
<222> LOCATION: (40)..(47)
<223> OTHER INFORMATION: Xaa can be any naturally occurring amino acid
<220> FEATURE:
<221> NAME/KEY: misc_feature
<222> LOCATION: (49)..(51)
<223> OTHER INFORMATION: Xaa can be any naturally occurring amino acid
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (59)..(60)
<223> OTHER INFORMATION: Xaa can be any naturally occurring amino acid
<220> FEATURE:
<221> NAME/KEY: misc_feature
```

```
<222> LOCATION: (63)..(64)
<223> OTHER INFORMATION: Xaa can be any naturally occurring amino acid
<220> FEATURE:
<221> NAME/KEY: misc_feature
<222> LOCATION: (67)..(69)
<223> OTHER INFORMATION: Xaa can be any naturally occurring amino acid

<400> SEQUENCE: 1

Cys Xaa Xaa Cys Xaa Xaa Asp Xaa Ala Xaa Gly Xaa Tyr Xaa Xaa Xaa
1               5                   10                  15

Xaa Cys Xaa Xaa Cys Leu Xaa Phe Phe Xaa Arg Xaa Xaa Xaa Xaa Xaa
            20                  25                  30

Xaa Xaa Xaa Xaa Xaa Cys Xaa Xaa Xaa Xaa Xaa Xaa Xaa Xaa Xaa Cys
        35                  40                  45

Xaa Xaa Xaa Lys Xaa Xaa Arg Xaa Xaa Cys Xaa Xaa Cys Arg Xaa Xaa
    50                  55                  60

Lys Cys Xaa Xaa Xaa Gly Met
65                  70

<210> SEQ ID NO 2
<211> LENGTH: 138
<212> TYPE: PRT
<213> ORGANISM: Homo sapiens

<400> SEQUENCE: 2

Met Pro Asn Phe Ser Gly Asn Trp Lys Ile Ile Arg Ser Glu Asn Phe
1               5                   10                  15

Glu Glu Leu Leu Lys Val Leu Gly Val Asn Val Met Cys Arg Lys Ile
            20                  25                  30

Ala Val Ala Ala Ala Ser Lys Pro Ala Val Glu Ile Lys Gln Glu Gly
        35                  40                  45

Asp Thr Phe Tyr Ile Lys Thr Ser Thr Thr Val Arg Thr Thr Glu Ile
    50                  55                  60

Asn Phe Lys Val Gly Glu Glu Phe Glu Glu Gln Thr Val Asp Gly Arg
65                  70                  75                  80

Pro Cys Lys Ser Leu Val Lys Trp Glu Ser Glu Asn Lys Met Val Cys
            85                  90                  95

Glu Gln Lys Leu Leu Lys Gly Glu Gly Pro Lys Thr Ser Trp Thr Arg
        100                 105                 110

Glu Leu Thr Asn Asp Gly Glu Leu Ile Leu Thr Met Thr Ala Asp Asp
    115                 120                 125

Val Val Cys Thr Arg Val Tyr Val Arg Glu
    130                 135

<210> SEQ ID NO 3
<211> LENGTH: 137
<212> TYPE: PRT
<213> ORGANISM: Homo sapiens

<400> SEQUENCE: 3

Met Pro Asn Phe Ala Gly Thr Trp Lys Met Arg Ser Ser Glu Asn Phe
1               5                   10                  15

Asp Glu Leu Leu Lys Ala Leu Gly Val Asn Ala Met Cys Arg Lys Val
            20                  25                  30

Ala Val Ala Ala Ala Ser Lys Pro His Val Glu Ile Arg Gln Asp Gly
        35                  40                  45

Asp Gln Phe Tyr Ile Lys Thr Ser Thr Thr Val Arg Thr Thr Glu Ile
    50                  55                  60
```

-continued

Asn Phe Lys Val Gly Glu Gly Phe Glu Glu Thr Val Asp Gly Arg
 65                  70                  75                  80

Lys Cys Arg Ser Leu Ala Thr Trp Glu Asn Glu Asn Lys Ile His Cys
                 85                  90                  95

Thr Gln Thr Leu Leu Glu Gly Asp Gly Pro Lys Thr Tyr Trp Thr Arg
            100                 105                 110

Glu Leu Ala Asn Asp Glu Leu Ile Leu Thr Phe Gly Ala Asp Asp Val
        115                 120                 125

Val Cys Thr Arg Ile Tyr Val Arg Glu
    130                 135

<210> SEQ ID NO 4
<211> LENGTH: 133
<212> TYPE: PRT
<213> ORGANISM: Homo sapiens

<400> SEQUENCE: 4

Met Val Asp Ala Phe Leu Gly Thr Trp Lys Leu Val Asp Ser Lys Asn
1               5                   10                  15

Phe Asp Asp Tyr Met Lys Ser Leu Gly Val Gly Phe Ala Cys Arg Gln
            20                  25                  30

Val Ala Ser Met Thr Lys Pro Thr Thr Ile Ile Glu Lys Asn Gly Asp
        35                  40                  45

Ile Leu Thr Leu Lys Thr His Ser Thr Phe Lys Asn Thr Glu Ile Ser
    50                  55                  60

Phe Lys Leu Gly Val Glu Phe Asp Glu Thr Thr Ala Asp Asp Arg Lys
65                  70                  75                  80

Val Lys Ser Ile Val Thr Leu Asp Gly Gly Lys Leu Val His Leu Gln
                85                  90                  95

Lys Trp Asp Gly Gln Glu Thr Thr Leu Val Arg Glu Leu Ile Asp Gly
            100                 105                 110

Lys Leu Ile Leu Thr Leu Thr His Gly Thr Ala Val Cys Thr Arg Thr
        115                 120                 125

Tyr Glu Lys Glu Ala
    130

<210> SEQ ID NO 5
<211> LENGTH: 132
<212> TYPE: PRT
<213> ORGANISM: Homo sapiens

<400> SEQUENCE: 5

Met Val Glu Ala Phe Cys Ala Thr Trp Lys Leu Thr Asn Ser Gln Asn
1               5                   10                  15

Phe Asp Glu Tyr Met Lys Ala Leu Gly Val Gly Phe Ala Cys Arg Gln
            20                  25                  30

Val Gly Asn Val Thr Lys Pro Thr Val Ile Ile Ser Gln Glu Gly Asp
        35                  40                  45

Lys Val Val Ile Arg Thr Leu Ser Thr Phe Lys Asn Thr Glu Ile Ser
    50                  55                  60

Phe Gln Leu Gly Glu Glu Phe Asp Glu Thr Thr Ala Asp Asp Arg Asn
65                  70                  75                  80

Cys Lys Ser Val Val Ser Leu Asp Gly Asp Lys Leu Val His Ile Gln
                85                  90                  95

Lys Trp Asp Gly Lys Glu Thr Asn Phe Val Arg Glu Ile Lys Asp Gly
            100                 105                 110

```
Lys Met Val Met Thr Leu Thr Phe Gly Asp Val Val Ala Val Arg His
        115                 120                 125
Tyr Glu Lys Ala
    130

<210> SEQ ID NO 6
<211> LENGTH: 132
<212> TYPE: PRT
<213> ORGANISM: Homo sapiens

<400> SEQUENCE: 6

Met Cys Asp Ala Phe Val Gly Thr Trp Lys Leu Val Ser Ser Glu Asn
1               5                   10                  15

Phe Asp Asp Tyr Met Lys Glu Val Gly Val Gly Phe Ala Cys Arg Lys
                20                  25                  30

Val Ala Gly Met Ala Lys Pro Asn Met Ile Ile Ser Val Asn Gly Asp
            35                  40                  45

Leu Val Thr Ile Arg Ser Glu Ser Thr Phe Lys Asn Thr Glu Ile Ser
    50                  55                  60

Phe Lys Leu Gly Val Glu Phe Asp Glu Ile Thr Ala Asp Asp Arg Lys
65                  70                  75                  80

Val Lys Ser Ile Ile Thr Leu Asp Gly Gly Ala Leu Val Gln Val Gln
                85                  90                  95

Lys Trp Asp Gly Lys Ser Thr Thr Ile Lys Arg Lys Arg Asp Gly Asp
            100                 105                 110

Lys Leu Val Val Glu Cys Val Met Lys Gly Val Thr Ser Thr Arg Val
        115                 120                 125

Tyr Glu Arg Ala
    130

<210> SEQ ID NO 7
<211> LENGTH: 132
<212> TYPE: PRT
<213> ORGANISM: Homo sapiens

<400> SEQUENCE: 7

Met Ser Asn Lys Phe Leu Gly Thr Trp Lys Leu Val Ser Ser Glu Asn
1               5                   10                  15

Phe Asp Asp Tyr Met Lys Ala Leu Gly Val Gly Leu Ala Cys Arg Lys
                20                  25                  30

Leu Gly Asn Leu Ala Lys Pro Thr Val Ile Ile Ser Lys Lys Gly Asp
            35                  40                  45

Ile Ile Thr Ile Arg Thr Glu Ser Thr Phe Lys Asn Thr Glu Ile Ser
    50                  55                  60

Phe Lys Leu Gly Gln Glu Phe Glu Glu Thr Thr Ala Asp Asn Arg Lys
65                  70                  75                  80

Thr Lys Ser Ile Val Thr Leu Gln Arg Gly Ser Leu Asn Gln Val Gln
                85                  90                  95

Arg Trp Asp Gly Lys Glu Thr Thr Ile Lys Arg Lys Leu Val Asn Gly
            100                 105                 110

Lys Met Val Ala Glu Cys Lys Met Lys Gly Val Val Cys Thr Arg Ile
        115                 120                 125

Tyr Glu Lys Val
    130

<210> SEQ ID NO 8
<211> LENGTH: 135
```

```
<212> TYPE: PRT
<213> ORGANISM: Homo sapiens

<400> SEQUENCE: 8

Met Ala Thr Val Gln Gln Leu Glu Gly Arg Trp Arg Leu Val Asp Ser
1               5                   10                  15

Lys Gly Phe Asp Glu Tyr Met Lys Glu Leu Gly Val Gly Ile Ala Cys
            20                  25                  30

Arg Lys Met Gly Ala Met Ala Lys Pro Asp Cys Ile Ile Thr Cys Asp
        35                  40                  45

Gly Lys Asn Leu Thr Ile Lys Thr Glu Ser Thr Leu Lys Thr Thr Gln
    50                  55                  60

Phe Ser Cys Thr Leu Gly Glu Lys Phe Glu Glu Thr Thr Ala Asp Gly
65                  70                  75                  80

Arg Lys Thr Gln Thr Val Cys Asn Phe Thr Asp Gly Ala Leu Val Gln
                85                  90                  95

His Gln Glu Trp Asp Gly Lys Glu Ser Thr Ile Thr Arg Lys Leu Lys
            100                 105                 110

Asp Gly Lys Leu Val Val Glu Cys Val Met Asn Asn Val Thr Cys Thr
        115                 120                 125

Arg Ile Tyr Glu Lys Val Glu
    130                 135

<210> SEQ ID NO 9
<211> LENGTH: 135
<212> TYPE: PRT
<213> ORGANISM: Homo sapiens

<400> SEQUENCE: 9

Met Pro Val Asp Phe Thr Gly Tyr Trp Lys Met Leu Val Asn Glu Asn
1               5                   10                  15

Phe Glu Glu Tyr Leu Arg Ala Leu Asp Val Asn Val Ala Cys Arg Lys
            20                  25                  30

Ile Ala Asn Leu Leu Lys Pro Asp Lys Glu Ile Val Gln Asp Gly Asp
        35                  40                  45

His Met Ile Ile Arg Thr Leu Ser Thr Phe Arg Asn Tyr Ile Met Asp
    50                  55                  60

Phe Gln Val Gly Lys Glu Phe Glu Glu Asp Leu Thr Gly Ile Asp Asp
65                  70                  75                  80

Arg Lys Cys Met Thr Thr Val Ser Trp Asp Gly Asp Lys Leu Gln Cys
                85                  90                  95

Val Gln Lys Gly Glu Lys Glu Gly Arg Gly Trp Thr Gln Trp Ile Glu
            100                 105                 110

Gly Asp Glu Leu His Leu Glu Met Arg Val Glu Gly Val Val Cys Lys
        115                 120                 125

Gln Val Phe Lys Lys Val Gln
    130                 135

<210> SEQ ID NO 10
<211> LENGTH: 135
<212> TYPE: PRT
<213> ORGANISM: Homo sapiens

<400> SEQUENCE: 10

Met Pro Pro Asn Leu Thr Gly Tyr Tyr Arg Phe Val Ser Gln Lys Asn
1               5                   10                  15

Met Glu Asp Tyr Leu Gln Ala Leu Asn Ile Ser Leu Ala Cys Arg Lys
```

-continued

```
                 20                  25                  30
Ile Ala Leu Leu Lys Pro Asp Lys Glu Ile Glu His Gln Gly Asn
             35                  40                  45

His Met Thr Val Arg Thr Leu Ser Thr Phe Arg Asn Tyr Thr Val Gln
 50                      55                  60

Phe Asp Val Gly Val Glu Phe Glu Asp Leu Arg Ser Val Asp Gly
 65                  70                  75                  80

Arg Lys Cys Gln Thr Ile Val Thr Trp Glu Glu His Leu Val Cys
                     85                  90                  95

Val Gln Lys Gly Glu Val Pro Asn Arg Gly Trp Arg His Trp Leu Glu
                100                 105                 110

Gly Glu Met Leu Tyr Leu Glu Leu Thr Ala Arg Asp Ala Val Cys Glu
            115                 120                 125

Gln Val Phe Arg Lys Val Arg
            130                 135

<210> SEQ ID NO 11
<211> LENGTH: 134
<212> TYPE: PRT
<213> ORGANISM: Homo sapiens

<400> SEQUENCE: 11

Met Thr Arg Asp Gln Asn Gly Thr Trp Glu Met Glu Ser Asn Glu Asn
 1               5                  10                  15

Phe Glu Gly Tyr Met Lys Ala Leu Asp Ile Asp Phe Ala Cys Pro Lys
             20                  25                  30

Ile Ala Val Arg Leu Thr Gln Thr Lys Val Ile Asp Gln Asp Gly Asp
             35                  40                  45

Asn Phe Lys Thr Lys Thr Thr Ser Thr Phe Arg Asn Tyr Asp Val Asp
 50                      55                  60

Phe Thr Val Gly Val Glu Phe Asp Glu Tyr Thr Lys Ser Leu Asp Asn
 65                  70                  75                  80

Arg His Val Lys Ala Leu Val Thr Trp Glu Gly Asp Val Leu Val Cys
                     85                  90                  95

Val Gln Lys Gly Glu Lys Glu Asn Arg Gly Trp Lys Gln Trp Ile Glu
                100                 105                 110

Gly Asp Lys Leu Tyr Leu Glu Leu Thr Cys Gly Asp Gln Val Cys Arg
            115                 120                 125

Gln Val Phe Lys Lys Lys
            130

<210> SEQ ID NO 12
<211> LENGTH: 134
<212> TYPE: PRT
<213> ORGANISM: Homo sapiens

<400> SEQUENCE: 12

Met Pro Ala Asp Leu Ser Gly Thr Trp Thr Leu Leu Ser Ser Asp Asn
 1               5                  10                  15

Phe Glu Gly Tyr Met Leu Ala Leu Gly Ile Asp Phe Ala Cys Arg Lys
             20                  25                  30

Ile Ala Lys Leu Leu Lys Pro Gln Lys Val Ile Glu Gln Asn Gly Asp
             35                  40                  45

Ser Phe Thr Ile His Thr Asn Ser Ser Leu Arg Asn Tyr Phe Val Lys
 50                      55                  60

Phe Lys Val Gly Glu Glu Phe Asp Glu Asp Asn Arg Gly Leu Asp Asn
```

-continued

```
            65                  70                  75                  80
Arg Lys Cys Lys Ser Leu Val Ile Trp Asp Asn Asp Arg Leu Thr Cys
                    85                  90                  95
Ile Gln Lys Gly Glu Lys Lys Asn Arg Gly Trp Thr His Trp Ile Glu
                100                 105                 110
Gly Asp Lys Leu His Leu Glu Met Phe Cys Glu Gly Gln Val Cys Lys
            115                 120                 125
Gln Thr Phe Gln Arg Ala
    130

<210> SEQ ID NO 13
<211> LENGTH: 132
<212> TYPE: PRT
<213> ORGANISM: Homo sapiens

<400> SEQUENCE: 13

Met Ala Phe Asp Ser Thr Trp Lys Val Asp Arg Ser Glu Asn Tyr Asp
1               5                   10                  15
Lys Phe Met Glu Lys Met Gly Val Asn Ile Val Cys Arg Lys Leu Ala
                20                  25                  30
Ala His Asp Asn Leu Lys Leu Thr Ile Thr Gln Glu Gly Asn Lys Phe
            35                  40                  45
Thr Val Lys Glu Ser Ser Ala Phe Arg Asn Ile Glu Val Val Phe Glu
        50                  55                  60
Leu Gly Val Thr Phe Asn Tyr Asn Leu Ala Asp Gly Thr Glu Leu Arg
65                  70                  75                  80
Gly Thr Trp Ser Leu Glu Gly Asn Lys Leu Ile Gly Lys Phe Lys Arg
                85                  90                  95
Thr Asp Asn Gly Asn Glu Leu Asn Thr Val Arg Glu Ile Ile Gly Asp
                100                 105                 110
Glu Leu Val Gln Thr Tyr Val Tyr Glu Gly Val Glu Ala Lys Arg Ile
            115                 120                 125
Phe Lys Lys Asp
    130

<210> SEQ ID NO 14
<211> LENGTH: 127
<212> TYPE: PRT
<213> ORGANISM: Homo sapiens

<400> SEQUENCE: 14

Met Ser Phe Ser Gly Lys Tyr Gln Leu Gln Ser Gln Glu Asn Phe Glu
1               5                   10                  15
Ala Phe Met Lys Ala Ile Gly Leu Pro Glu Glu Cys Ile Gln Lys Gly
                20                  25                  30
Lys Asp Ile Lys Gly Val Ser Glu Ile Val Gln Asn Gly Lys His Phe
            35                  40                  45
Lys Phe Thr Ile Thr Ala Gly Ser Lys Val Ile Gln Asn Glu Phe Thr
        50                  55                  60
Val Gly Glu Glu Cys Glu Leu Glu Thr Met Thr Gly Glu Lys Val Lys
65                  70                  75                  80
Thr Val Val Gln Leu Glu Gly Asp Asn Lys Leu Val Thr Thr Phe Lys
                85                  90                  95
Asn Ile Lys Ser Val Thr Glu Leu Asn Gly Asp Ile Ile Thr Asn Thr
                100                 105                 110
Met Thr Leu Gly Asp Ile Val Phe Lys Arg Ile Ser Lys Arg Ile
```

-continued

```
                115                 120                 125

<210> SEQ ID NO 15
<211> LENGTH: 128
<212> TYPE: PRT
<213> ORGANISM: Homo sapiens

<400> SEQUENCE: 15

Met Ala Phe Thr Gly Lys Phe Glu Met Glu Ser Glu Lys Asn Tyr Asp
1               5                   10                  15

Glu Phe Met Lys Leu Leu Gly Ile Ser Ser Asp Cys Ile Glu Lys Ala
            20                  25                  30

Arg Asn Phe Lys Ile Val Thr Glu Val Gln Gln Asp Gly Gln Asp Phe
        35                  40                  45

Thr Trp Ser Gln His Tyr Ser Gly Gly His Thr Met Thr Asn Lys Phe
    50                  55                  60

Thr Val Gly Lys Glu Ser Asn Ile Gln Thr Met Gly Gly Lys Thr Phe
65                  70                  75                  80

Lys Ala Thr Val Gln Met Glu Gly Gly Lys Leu Val Val Asn Phe Pro
                85                  90                  95

Asn Tyr His Gln Thr Ser Glu Ile Val Gly Asp Lys Leu Val Glu Val
            100                 105                 110

Ser Thr Ile Gly Gly Val Thr Tyr Glu Arg Val Ser Lys Arg Leu Ala
        115                 120                 125
```

COMPOSITIONS AND METHODS FOR MEASURING NUCLEAR RECEPTOR LIGANDS

RELATED APPLICATIONS

The present application claims priority to and the benefit of U.S. Provisional Application 60/634,764, filed Dec. 9, 2004.

GOVERNMENTAL SUPPORT

The present invention was supported in part by a grant from the National Institutes of Health, RO1 CA68150. Therefore, the government has certain rights to this invention.

FIELD OF THE INVENTION

The present invention relates to nuclear hormone receptors, intracellular lipid binding proteins (iLBP), and their intracellular binding ligands. In particular, the invention pertains to detecting and measuring the concentration of ligand that binds to their cognate nuclear receptors and iLBPs.

BACKGROUND OF THE INVENTION

One method for cells receiving signals from the external environment is through ligand-receptor interactions. In one scenario, the receptor is integral to the cell and is embedded within the plasma membrane bilayer of the cell. The receptor may traverse the entire bilayer or reside within the layer having a portion of it exposed on the surface of the cell. Typical ligands that interact with these receptors are hydrophilic molecules. Through this interaction, secondary events are triggered leading to changes within the cytosol of the cell such as protein phosphorylation.

In contrast to hydrophilic ligands, hydrophobic molecules, such as steroid and thyroid hormones, pass through the plasma membrane of a cell and interact with specific receptor proteins residing within the cytoplasm or nucleus. Other hydrophobic molecules, such as retinoic acid, are metabolically synthesized in the cell itself. Similarly to externally derived hydrophobic molecules, hydrophobic compounds that are synthesized intracellularly interact with intracellular receptor proteins to exert their biological effects.

For example, steroid hormones (testosterone, estrogen, etc.) dissociate from plasma-binding proteins and cross the plasma membrane and enter target cells. Steroid hormone receptors are tissue-specific binding proteins found in low concentrations in the cytoplasm of the cell. When steroid receptors are occupied by ligand they change conformation and become activated with enhanced affinity for nuclear chromatin. The activated hormone-receptor complex accumulates in the nucleus bound to chromosomal DNA containing acceptor sites for the complex. The high affinity interaction of the steroid-hormone receptor complex with nuclear chromatin results in activation of DNA transcription and in the synthesis of specific mRNAs.

Hydrophobic ligands other than steroids similarly bind to and activate different nuclear receptors. For example, the receptors for thyroid hormones are found in the nucleus even in the absence of their ligand. Thyroid hormones enter cells and travel to the nucleus. Specific genes are under thyroid hormone control, and they are transcribed to particular mRNA in response to this ligand. In turn, translation of the mRNA results in the synthesis of specific cell proteins.

In addition to nuclear receptors, hydrophobic ligands bind in cells to proteins that are members of a family of homologous proteins termed intracellular lipid binding proteins (iLBPs). These proteins reside in the cytosol of cells. Some iLBPs move to the nucleus when they bind their cognate ligands. For example, the iLBP called adipocyte fatty acid binding protein (adipocyte FABP) moves from the cytosol to the nucleus following binding of its cognate ligands. Intracellular lipid binding proteins often share ligands with particular nuclear receptors. For example, the anti-diabetic drug troglitazone binds to the nuclear receptor termed peroxisome proliferator activated receptor γ (PPARγ) and also associates with adipocyte FABP.

Another example of nuclear receptor ligands are the vitamin A metabolites retinoic acids ("RA") and their synthetic derivatives, collectively known as retinoids, which can be used in the treatment of a variety of pathologies ranging from dermatological disorders to cancer.

The retinoid members of the nuclear hormone receptor superfamily are responsive to compounds referred to as retinoids, which include retinoic acid and a series of natural and synthetic derivatives which have been found to exert profound effects on development and differentiation in a wide variety of systems.

Retinoic acid-dependent transcription factors, referred to as RARs (retinoic acid receptors), have been identified. Currently, three different RAR subtypes (alpha, beta and gamma) and several isoforms of each are known to exist in mammals. RARs share sequence homology with other members of the superfamily of nuclear hormone receptors. This family of proteins encompasses ligand-dependent transcription factors that regulate the expression of particular target genes upon binding of specific ligands. Different RAR subtypes are expressed in distinct patterns throughout development and in the mature organism.

Additional members of the nuclear hormone superfamily of receptors that respond to retinoids have been identified. These are termed retinoid X receptors (RXRs): RXR-α (see Mangelsdorf et al., in Nature 345: 224-229 (1990)), RXR-β (see Hamada et al., Proc. Natl. Acad. Sci. USA 86: 8289-8293 (1989)), and RXR-γ (see Mangelsdorf et al., Genes and Development 6:329-344 (1992)).

Although both RARs and RXRs respond to retinoic acids, these receptors differ in several important aspects. First, RAR and RXR are significantly divergent in primary structure. These sequence differences are reflected in differential responsiveness of RAR and RXR to various vitamin A metabolites and synthetic retinoids. In addition, distinctly different patterns of tissue distribution are seen for RAR and RXR. Furthermore, while RXR can activate transcription as a homodimer, i.e. on its own, the transcriptional activity of RAR is mediated through RAR-RXR heterodimers. Finally, RXR homodimers bind to response elements that are distinct from the DNA sequences that are recognized by RAR-RXR heterodimers, and thus RXR-RXR and RXR-RAR complexes regulate the expression of different genes.

Retinoid therapy is complicated by the toxicity of these compounds at pharmacological doses. Existing methods for retinoid detection and quantification consist of organic solvent extractions and HPLC analyses, procedures that are too time-consuming and expensive to be used in the hospital/clinic setting. Consequently, as currently practiced, retinoid treatment is not individualized for particular patients but is administered by 'standard' dosing. This is so despite the high toxicity of these compounds and the large patient-to-patient variability in resulting plasma concentrations of RA.

Certain diseases affect or are affected by processes that alter physiological events that are associated with specific ligand-receptor interactions. Clearly, the detection and quantitation of ligands that bind to nuclear receptors is important diagnostically as well as for monitoring physiological effects during a treatment regime.

SUMMARY OF THE INVENTION

The present invention relates to nuclear receptors, intracellular lipid binding proteins, and their cognate intracellular binding ligands. Embodiments of the present invention are directed toward detecting and quantitating ligands of nuclear receptors and intracellular lipid binding proteins. In particular, the present invention pertains to methods designed to measure ligands whose cognate receptor resides intracellularly, either in the cytoplasm or in the nucleus of a cell. In one particular aspect, the receptors are nuclear hormone receptors. In another aspect, the receptors are intracellular lipid binding proteins. The methods of the present invention are directed to detecting and measuring ligands from various different source materials.

One embodiment of the present invention is directed to the detection and measurement of a ligand from a sample. In one aspect of this embodiment, the sample preparation comprises a homogenous ligand preparation. In another aspect, the sample comprises a heterogeneous composition of ligands, wherein the population of ligands differ in their affinity for a particular receptor protein (also referred to as a sensor protein). In this embodiment, a titration curve is established using known quantities of a standard ligand that interacts with a known receptor protein. For example, the ligand can be retinoic acid and the receptor can be a retinoid nuclear receptor or a cellular retinoic acid binding protein. Typically, the receptor protein is labeled prior to incubation with a ligand. Following the establishment of a titration curve, the sample containing a putative ligand can be admixed with the labeled receptor protein preparation. The signal generated following this incubation can be compared to the titration curve in order to ascertain the concentration of the sample ligand. The receptor used for establishing the standard curve is typically the same receptor used in the assay of the sample ligand.

Another embodiment of the present invention is directed to the screening of ligands that bind to nuclear receptors and to measurements of the binding affinities of such ligands. In one aspect of this embodiment, synthetic compounds that potentially serve as therapeutic agents, acting either as activators or inhibitors of particular receptors, are tested for their capacity for receptor binding.

BRIEF DESCRIPTION OF THE DRAWINGS

For a better understanding of the present invention, reference in the detailed description is made to the accompanying figures, wherein:

FIG. 2A shows the amino acid sequences of mutants of intracellular lipid binding proteins to be used as sensor proteins to detect and measure different cognate ligands; * indicates mutation point; B is a Table of names and accession numbers iLBPs and exact nature of point mutations;

DETAILED DESCRIPTION OF THE INVENTION

Figure 1:
FIG. 1 illustrates the position of L29 residue of the CRABP-I protein in the (B) absence (apo) and (A) presence (holo) retinoic acid; there is a shift in position of L29 upon binding of retinoic acid.

The present invention relates to nuclear receptors, intracellular lipid-binding proteins (iLBP), and their intracellular binding ligands. Embodiments of the present invention are directed toward detecting and quantitating ligands of nuclear receptors and iLBPs. In particular, the present invention pertains to methods designed to measure ligands whose cognate receptor resides within a cell. The methods of the present invention are directed to detecting and measuring ligands which can originate from a variety of different source materials. Another embodiment of the present invention is directed towards identification and screening of ligands that potentially bind to nuclear receptors and to measurements of their receptor binding affinities. In particular, the methods serve to test whether natural or synthetic compounds can bind to a particular receptor and enable ready screening of multiple compounds.

There is significant homology between the various known nuclear hormone receptors. The super-family of nuclear receptors is comprised of hormone binding proteins that operate as ligand-dependent transcription factors. The family contains several branches including steroid receptors, receptors that belong to the retinoid/thyroid class, and receptor for which specific ligands have not yet been identified. These hormone binding proteins have the intrinsic ability to bind to specific DNA sequences. Following binding, the transcriptional activity of target gene (i.e., a gene associated with the specific DNA sequence) is modulated as a function of the ligand bound to the receptor.

The DNA-binding domains of all of these nuclear receptors are related, consisting of 66-68 amino acid residues, and possessing about 20 invariant amino acid residues, including nine cysteines. See, U.S. Pat. No. 6,576,676, the entire teaching of which is incorporated herein by reference.

A member of the superfamily can be identified as a protein which contains the above-mentioned invariant amino acid residues, which are part of the DNA-binding domain of steroid receptors such as the human glucocorticoid receptor (amino acids 421-486), the estrogen receptor (amino acids 185-250), and the mineralocorticoid receptor (amino acids 603-668), and retinoid/thyroid receptor-like proteins such as the human retinoic acid receptor (amino acids 88-153). The highly conserved amino acids of the DNA-binding domain of members of the superfamily are as follows:

Cys-X-X-Cys-X-X-Asp*-X-Ala*-X-Gly*-X-Tyr*-X-X-X-X-Cys-X-X-Cys-Lys*-X-Phe-Phe-X-Arg*-X-X-X-X-X-X-X-X-X-(X-X-) Cys-X-X-X-X-X-(X-X-X-) Cys-X-X-X-Lys-X-X-Arg-X-X-Cys-X-X-Cys-Arg*-X-X-Lys*-Cys-X-X-X-Gly*-Met (SEQ ID No 1), wherein X designates non-conserved amino acids within the DNA-binding domain; the amino acid residues denoted with an asterisk are residues that are almost universally conserved, but for which variations have been found in some identified hormone receptors; and the residues enclosed in parenthesis are optional residues (thus, the DNA-binding domain is a minimum of 66 amino acids in length, but can contain several additional residues).

Members of the nuclear hormone superfamily of receptors include steroid receptors such as glucocorticoid receptor, mineralocorticoid receptor, progesterone receptor, androgen receptor, and the like; plus thyroid/retinoid-like receptors such as retinoid receptors (RAR-α, RAR-β, RAR-γ receptors, and the like), plus RXR-α, RXR-β, RXR-γ receptors, and the like; thyroid receptors, such as TR-α, TR-β, and the like; the vitamin D receptor as well as other gene products which, by their structure and properties, are considered to be members of the superfamily. For a comprehensive list of nuclear receptor family members see: The Nuclear Receptor FactsBook, Laudet, V. and Gronemeyer, H. 2002, Academic Press, London and San Diego, the entire teaching of which is incorporated herein by reference.

In addition to binding to nuclear receptors, hydrophobic ligands associate in cells with members of the family of homologous proteins known as Intracellular Lipid Binding Proteins (iLBP). Members of this family are small soluble proteins of a molecular weight of about 15 kDa. The iLBPs can be recognized by their highly conserved three dimensional structure. These proteins are comprised of a structure termed beta-clam, in which two 5-stranded beta sheets are arranged orthogonally to form a ligand binding pocket. In iLBPs, a single helix-loop-helix "lid" is situated over the entrance to the ligand binding pocket and appears to limit access to the pocket. Although similar in structure, iLBPs bind different hydrophobic molecules with distinct selectivities. For example, this family includes cellular retinol binding proteins (CRBPs) that bind retinol and retinaldehyde, cellular retinoic acid binding proteins (CRABPs) that associate with retinoic acid, and multiple forms of fatty acid binding proteins (FABPs) that bind a variety of fatty acids, metabolic derivatives of fatty acids such as prostaglandins, and other hydrophobic ligands.

One embodiment of the present invention is directed to the detection and measurement of a ligand from a sample. In one aspect of this embodiment, the sample preparation comprises a homogenous ligand preparation. In another aspect, the sample comprises a heterogeneous composition of ligands, wherein the population of ligands differ in their affinity for a particular receptor protein. In this embodiment, a titration curve is established using known quantities of a standard ligand that interacts with a known nuclear receptor protein. For example, the ligand can be retinoic acid and the receptor can be a retinoid receptor. Typically, the receptor protein is labeled by methods well known to those skilled in the art prior to incubation with a ligand. Following the establishment of a titration curve, the sample containing a putative ligand can be admixed with the labeled receptor protein preparation. The signal generated following this incubation can be compared to the titration curve in order to determine the concentration of the sample ligand. The receptor used for establishing the standard curve is typically the same receptor used in the assay of the sample ligand.

A standard titration curve must first be established. To accomplish this goal, the receptor protein must be labeled with, e.g., with a fluorescent label, using methods well known to those skilled in the art. One example of a suitable label is fluorescein. Other forms of labeling well known to those skilled in the art can also be employed, e.g., use of radioactive labels. The receptor protein serves as a sensor and can be referred to as a sensor protein. A known quantity of labeled sensor protein can be aliquoted into several vials. The sensor protein should be in a suitable buffer such that its affinity to its cognate ligand will be preserved. An example of such a buffer comprises about 20 mM Hepes, ~pH 8.0, about 100 mM KCl, about 1 mM EDTA, and about 1 mM dithiothreitol (DTT). The buffer may vary depending upon the sensor protein used.

Next, using predetermined concentrations, a suitable ligand can be added, under conditions suitable for affinity binding, to the various vials containing the sensor protein. Each vial receiving a different ligand concentration. For example, the sensor protein may be present at concentrations ranging between 0.05 and 1 μM. Ligand can then be added at concentrations in that range between 1/10 to 2-fold of the protein concentration. In this range, a complete titration curve can be obtained. As ligand-protein association rates are rapid, measurements can be carried out immediately following mixing. The source of the ligand can be from a commercial source, alternatively, the ligand can be synthesized using an intact or extract cell system or an automated platform.

The labeled sensor protein has a particular emission signal absent any ligand. When the ligand interacts with and binds to the sensor, the signal changes. The interaction between the ligand and sensor induces a detectable signal change in, e.g., fluorescence. For example, as the concentration of ligand increases, the signal elaborated from the labeled sensor diminishes due to conformational changes in the sensor protein. Other patterns in signal elaboration are considered to be within the scope of the present invention. Regardless of the signal platform employed, it is important that a relationship exist between signal elaboration and changes in ligand concentration and that such relationship can be exploited in order to detect and measure ligand.

A standard titration curve can then be established. (See the Example below for a typical titration curve using the methods of the present invention.) It is this standard curve that can be used to ascertain the concentration of a ligand within a sample.

In order to ascertain if a particular sample comprises a ligand and, if so, the quantity of the ligand, an aliquot of sample can be added to a vial comprising the labeled sensor protein. The sensor protein in the reaction vial should be under the same or analogous conditions to those which were used to generate the standard curve. The presence of a ligand in the sample can be inferred from a change in spectral emission. Additionally, the quantity of the ligand can be computed using the titration curve previously established.

In the present embodiment, the sample includes, but is not limited to, tissue and cell extracts from animal and plant. The sample includes biological fluids such a sera, urine, aqueous humor, vitreous, bodily excretions, blood and alike. Tissues such as kidney, liver, lung, eye, muscle, and intestine can serve as sources for the biological sample. Mammals such as human, rodent, sheep, pig, cow and alike can serve as sources for the biological sample. Established cell lines, such as carcinoma cells and primary cells in culture, can serve as sources for the biological sample.

Suitable ligands for the present embodiment include, but are not limited to, ligands that bind to a nuclear receptor protein and ligands that bind to intracellular lipid binding proteins. These ligands can be natural or synthetically produced. Ligands of the present embodiment include modifications and derivatives of parent ligands. Modified ligands include, but are not limited to, chemically modified ligands. Derivatives include fragments of a parent ligand in which the fragment demonstrates affinity for the parent's cognate receptor. This principle holds true for any modified or derived ligand, i.e., there has to be a discriminating affinity between the ligand and the receptor. The affinity need not match that of the parents, however, it has to be sufficient enough so as to be useful in the present invention. Agonists are also within the scope of this invention. In some instances, agonists can be understood as derivatives or modifications of parent ligands.

Suitable receptors for the present embodiment include, but are limited to, receptors that reside within the interior of a cell. Nuclear receptors and iLBPs are included within this definition of suitable receptors. Examples of such receptors include, but are not limited to, estrogen receptors, glucocorticoid receptors, thyroid hormone receptors, vitamin D receptors, CRABPs, CRBPs, and the like. Receptors can be isolated from nature or can be recombinantly produced using techniques well known to those skilled in the art. Receptors of the present embodiment need not have the complete complement of amino acid residues as found in nature. In one aspect, the receptors can have a percent homology ranging from about 95% to about 100%, in still another aspect, the percent homology can range from about 85% to about 95%, in still a further aspect, the percent homology can range from about 75% to about 85%, and in still another aspect, the percent homology can range from about 65% to about 75%. Derived receptors include those proteins having the same or similar affinity for a ligand as the parent but differ in their chemical structure. Their structure can be a truncated form or a structure that has been modified by the addition of one or more chemical moieties. Derived receptors include, but are not limited to, protein fragments that have a reduced complement as compared to the parent. Receptors of the present embodiment include those receptors that have been modified by, for example, the addition of one or more moieties. These moieties include, but are not limited to, nucleic acids, small organic molecules, protein-based molecules, lipids, and alike. Receptors of the present embodiment also include receptors that have been modified by mutations, such as replacing, deleting, or adding particular amino acid residues.

In one aspect, receptors of the present embodiment are labeled with a molecule capable of elaborating a signal. For example, a suitable label includes a fluorescence label. In a particular aspect, the fluorescent probe used is fluorescein. However, one skilled in the art will appreciate that other labels can be employed, see, e.g., Hermanson, G., 1996, Bioconjugate Techniques, Academic Press; Butcher, E. C. et al., 1960 J. Immunol. Methods 37:109; Chen, R. F. 1969 Arch. Biochem. Biophys. 133:263-276, the entire teachings of which are incorporated herein by reference. (For labeling procedures and an array of available fluorescent probes see: Haugland R. P. 2002, Molecular Probes, Handbook of fluorescent probes and research products. $9^{th}$ edition, the teaching of which is hereby incorporated by reference.)

One embodiment of the present invention is directed to the measurement of retinoids, including, but not limited to, any and all derivatives such as all-trans-retinoic acid. The sensor proteins employed for this method include RAR, CRABP-I and II, and the like.

The biological activities of retinoids stem from their ability to regulate transcription of multiple target genes. Two classes of proteins are involved in these activities. One class is comprised of transcription factors that are activated by retinoids, i.e., the retinoic acid receptors (RAR). These receptors are activated by both all-trans-retinoic acid (RA) and 9-cis-retinoic acid (9cRA). The other class comprises retinoid X receptors (RXR), which are activated by 9cRA.

Exemplary receptors which are responsive to retinoids, natural or synthetic compounds as defined herein, include RAR-alpha, RAR-beta, RAR-gamma, and splicing variants encoded by the genes for such receptors, as well as various combinations thereof (i.e., homodimers, heterodimers, and the like), including combinations of such receptors with other members of the nuclear receptor super-family with which the retinoid receptors can interact by forming heterodimers. For example, the retinoic acid receptor-α can form a heterodimer with retinoid X receptor-α, the retinoic acid receptor-β can form a heterodimer with retinoid X receptor-α, retinoic acid receptor-γ can form a heterodimer with retinoid X receptor-α, retinoid X receptor-α can form a heterodimer with thyroid receptor, retinoid X receptor-β can form a heterodimer with vitamin D receptor, retinoid X receptor-γ can form a heterodimer with retinoic acid receptor-α, and the like. Another class of receptors that are responsive to retinoids are the iLBPs including CRABP-I, CRABP-II, the keratinocyte fatty acid binding protein.

In addition to the naturally occurring retinoids such as all-trans-retinoic acid, 9-cis-retinoic acid, 4-oxo-retinoic acid, and the like, various synthetic ligands that selectively activate either RAR (retinoids) or RXR (rexinoids) have been developed and are in current therapeutic use in a variety of disease states. In addition to associating with receptors, RA binds in cells to proteins known as cellular retinoic acid-binding proteins (CRABP-I and CRABP-II). The CRABPs bind RA, but they do not associate with rexinoids. The present methods exploit the ligand selectivities of retinoid receptors and binding proteins using CRABPs and RAR to quantify retinoids, and RXR to measure the concentrations of 9cRA and synthetic rexinoids.

In order to utilize these proteins (CRABPs, RAR, RXR, and alike) as 'sensors', the proteins are covalently labeled with, for example, environmentally-sensitive fluorescent probes using commercially available reagents. However, one skilled in the art will appreciate that other commercially available labels can also be employed such as labels having one or more radioactive moieties. The resulting labeled sensor proteins retain their ligand-binding properties and display absorption and emission peaks at long wavelengths (~500 nm), a range in which optical interference from biological samples is minimal. Due to the environmental sensitivity of the probe (assuming that an appropriate label is employed), association of the label (e.g., fluorescent) sensor proteins with appropriate ligands leads to distinct changes in their signal (e.g., fluorescence intensity or spectrum), which are used to monitor the interaction.

One embodiment of the present invention is directed to the measurement of rexinoids including 9-cis-retinoic acid, including, but not limited to, any and all derivatives or other compounds that bind to RXR such as docosahexaenoic acid. The sensor proteins employed for this method include RXR, and alike. Protocols for using RXR as a sensor for rexinoids are essentially identical to the one described below except for the usage of labeled RXR in place of CRABP.

In one embodiment, sensor proteins were generated as mutants viz. wild-type in order to optimize labeling conditions. Although representative calibration curves are illustrated herein, the dynamic range of the measurements can be adjusted to accommodate different concentration ranges by changing the concentration of sensor proteins used in a particular assay. For example, using a sensor protein concentration of ~1 µM allows for reliable measurements of one or more ligands at concentrations ranging from 100 nM to about 800 nM (a range that is appropriate for measurements of serum levels of retinoids observed during therapy, Lanvers, C.

et al. 2003, Med. Pediatr. Oncol., 40:293-301, the entire teaching of which is incorporated herein by reference). However, scaling the concentrations of sensor proteins used in the present methods can accommodate a much wider range of retinoid concentrations. For example, using a sensor protein concentration of 50 nM allows for measurements of ligand concentration in the range of 5 nM to 40 nM.

In one embodiment, the sensor protein is selected from the family of intracellular lipid binding proteins (iLBP), for example, cellular CRABP-I or CRABP-II. The iLBPs, including CRABPs, lack reactive residues that allow for efficient labeling. To overcome this difficulty, mutants (derivatives) of these proteins can be generated. As shown in FIGS. 1 (a) and (b), L29 is an amino acid residue of the CRABP-I sensor protein that undergoes conformation change upon ligand-receptor interaction. FIGS. 2 (a) and (b) shows the amino acid sequences of mutant CRABPs and other intracellular lipid binding proteins and highlights the residues that undergo conformation change upon ligand-protein interactions. In the mutants, the native residue in this position is replaced by a cysteine to allow for efficient labeling.

Residue L29 in both CRABP-I and CRABP-II was replaced with a cysteine. Recombinant mutant proteins, tagged with either GST or hexahistidine, are over-expressed in *E. coli* and purified by affinity chromatography using standard methodologies. (For purification of hexahistidine-tagged proteins see: The Recombinant Protein Handbook: Protein Amplification and Simple Purification, 2002, Amersham Biosciences, 18-1142-75, pp. 41-58; Nieba, L. et al., 1997, Anal Biochem 252, 217-228 (1997). For purification of GST-fusion proteins see: Smith, D. B. and Johnson, K. S., 1988, Gene 67, 31. Parker, M. W. et al., 1990, J. Mol. Biol. 213:221; Ji, X. et al., 1992, Biochemistry 31, 10169; the entire teachings of which are incorporated herein by reference).

Figure 3:
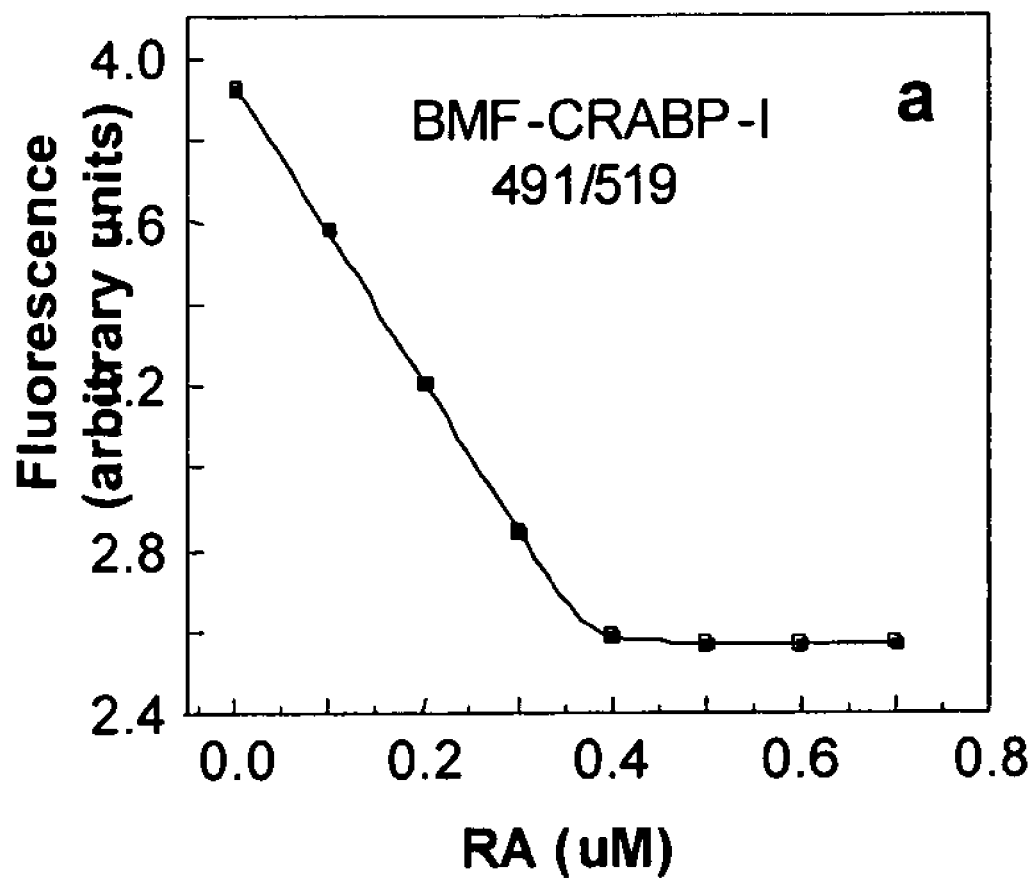
FIG. 3 is a titration plot of fluorescein-labeled mutant (L29C) CRABP-I with all trans-retinoic acid.

Purified proteins can be labeled with a label such as the fluorescent probe fluorescein using a commercially available reagent (bromomethyl fluorescein), see, Stefanova, et al., 1993, Biochemistry 32:6095-6103, the entire teaching of which is incorporated herein by reference. FIG. 3 depicts a representative assay in which labeled-CRABP-I is used to detect RA at the 10-100 nM range. Similar results can be obtained using labeled CRABP-II.

In another embodiment, the sensor protein is RAR. RAR can be used as an additional tool for measuring retinoid concentrations. For high-yield bacterial expression, the protein of choice is a truncated form of the receptor comprised of its ligand-binding domain. This is labeled with, for example, fluorescein. In the case of RAR, the 'readout' may be comprised of monitoring fluorescence energy transfer between the bound RA and the fluorophore ($\lambda$excitation=360 nm; $\lambda$emission=520 nm), or monitoring changes in the direct fluorescence of the probe ($\lambda$excitation=490 nm, $\lambda$emission=515 nm).

Figure 4:
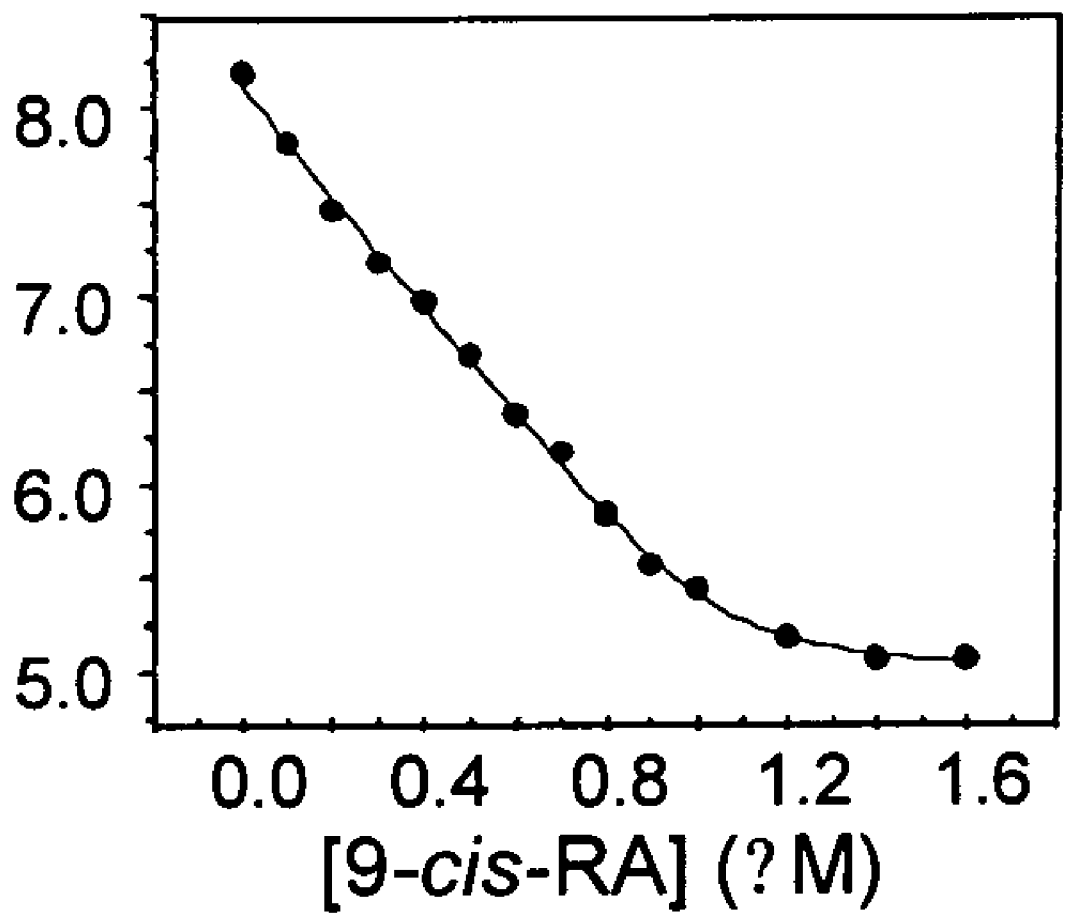
FIG. 4 is a titration plot of fluorescein-labeled mutant RXR with 9-cis-RA; ligand binding was followed by monitoring changes in the fluorescence of the labeled protein ($\lambda$ex—490 nm; $\lambda$em.—517 nm)

In yet another embodiment, the sensor protein is RXR. RXR can serves as a selective tool for measuring rexinoids. A complication in utilizing this protein is that the wild-type receptor self-associates into high affinity homotetramers, which, in turn, dissociates upon binding of ligand. Consequently, titrations of labeled RXR with rexinoids result in complex curves. To overcome this difficulty, an RXR mutant that does not form tetramers is used, see, RXR$\alpha$F443A/F444A, see Kersten, S. et al. 1995, Biochemistry, 34:13717-13721; Kersten, S. et al. 1995, Biochemistry, 34:14263-14269, the entire teachings of which are incorporated herein by reference. The recombinant mutant is purified from over-expressing *E. coli* as a GST-tagged or hexa-histidine-tagged protein and labeled with fluorescein. FIG. 4 shows a representative calibration curve for the natural rexinoid 9-cis-RA. Ligand-binding was followed by monitoring changes in the fluorescence of the labeled sensor protein ($\lambda$ excitation=490 nm, and $\lambda$ emission=517 nm). Additional experiments showed that this reagent can be similarly used to measure concentrations of the synthetic RXR ligand bexarotene (Targretin).

Example

An example of performing a method of the present invention for measuring retinoic acid concentrations is detailed below. In this example, the CRABP-I mutant CRABP-I-L29C was employed and labeled with BMF. The labeled receptor protein was used to measure retinoic acid concentrations in cultured cells.

MCF-7 cells were cultured on 60 mm plates in DMEM containing 5% charcoal-treated FBS until reaching 75-90% confluence. Media was then changed to serum free DMEM and cells were treated with retinoic acid. Following treatment, media were removed and replenished with media devoid of retinoic acid. At different time points, cells washed twice in 2 ml phosphate-buffered saline (PBS, pH 7.4). Cells were scraped, resuspended in 1 ml PBS and pelleted by centrifugation. PBS was removed and the cell pellet resuspended in ethanol. The suspension was placed at −20° C. overnight. Cells were then centrifuged, and the supernatant (ethanol extract), containing retinoic acid was stored at 20° C. until use. Cell pellet was resuspended in 1 M NaOH and protein content was measured by the Bradford assay.

Figure 5:
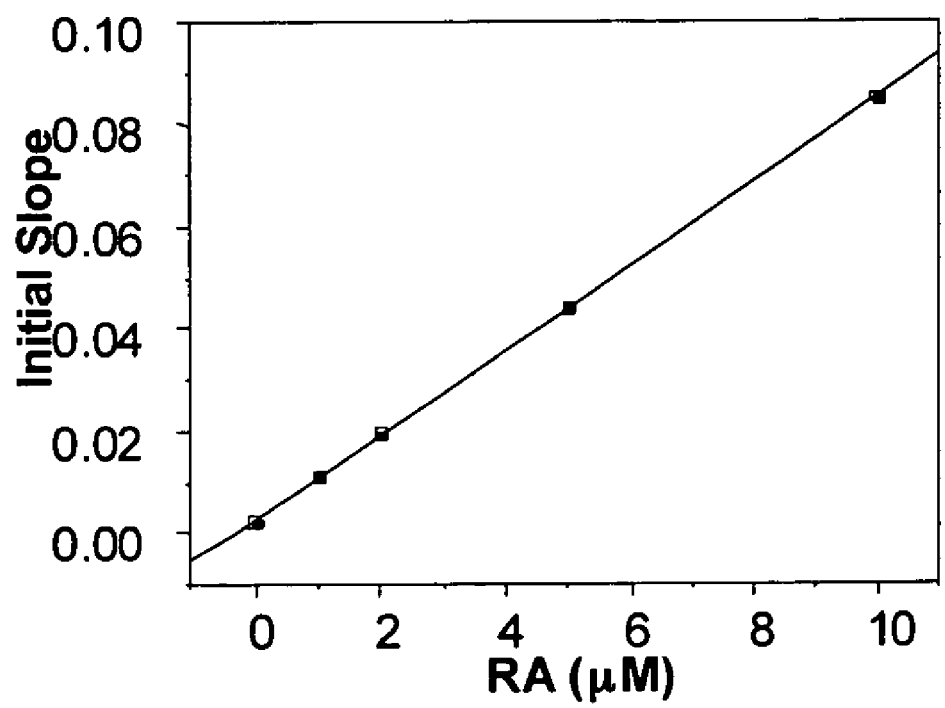
FIG. 5 is a calibration curve for use in measurements of retinoic acid in cell extracts using fluorescein-labeled CRABP-I-L29C; it shows a linear relationship between initial slopes of titrations of mutant BMF-CRABP-I and concentration of retinoic acid in standard solutions.

BMF-CRABP-I-L29C (in 20 mM Hepes, pH 8.0, 100 mM KCl, 1 mM EDTA, 1 mM DTT) was placed in a cuvette and titrated with a standard retinoic acid solution in ethanol. RA was added, the cuvette was mixed, and the fluorescence recorded at room temperature. Different points on the titration curve were obtained by sequential addition of RA to the same cuvette. The titration was monitored using a spectrofluorometer by following the retinoic-acid induced change in the fluorescence of the protein-bound label ($\lambda$ex=494 nm; $\lambda$em=519 nm). To obtain a calibration curve that is consistent with the samples, standard retinoic acid solutions were obtained as follows: MCF-7 mammary carcinoma cells were plated at the same time and density as the test plates, and extracted like the test samples with the exception that known concentrations of retinoic acid were added to the ethanol prior to extraction to yield standard solutions. BMF-CRABP-I-L29C was titrated with each of the standard solutions to obtain individual titration curves similar to the one shown in FIG. 3. The resulting data were analyzed to obtain the initial linear slope for the progress of each of the standard titrations. These slopes were then plotted against the concentrations of RA in each standard solution to obtain a calibration curve (FIG. 5).

Figure 6:
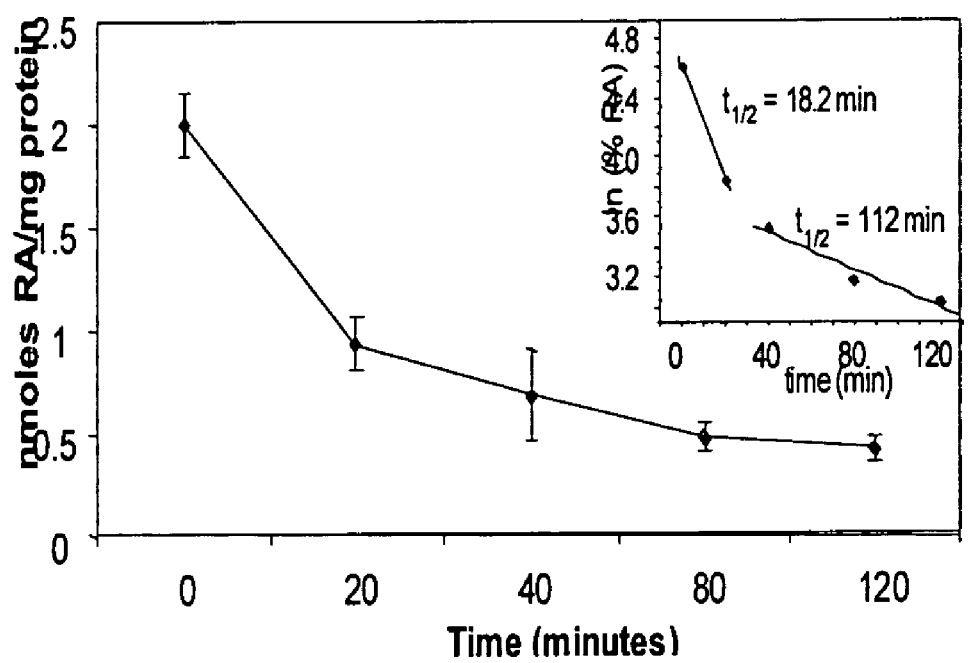
FIG. 6 is an example for using the protocol to measure the degradation of retinoic acid in cancer cells, a time course for disappearance of retinoic acid from mammary carcinoma MCF-7 cells is shown; MCF-7 cells were treated with 1 $\mu$M retinoic acid for 1 hour; Retinoic acid was removed from the media, cells were lysed in ethanol at the indicated times, and retinoic acid concentrations were monitored using the BMF-CRABP-I-L29C assay; Inset shows the same data plotted on a log scale to extract the half-life of the compound in the cells.

The labeled protein was titrated with each test sample to obtain an initial slope. Using the calibration curve, the total retinoic acid in the test sample was then calculated. The amount of RA in each sample was expressed as pmoles retinoic acid per mg protein. A time course for degradation of retinoic acid in MCF-7 cells following a 1 hour-term treatment with RA is shown in FIG. 6.

Another embodiment is directed towards testing the association of ligands with a particular receptor. In one aspect of this embodiment, the method is used to determine the ability of potential ligands to bind to a receptor. Test compounds include known receptor ligands and novel potential ligands obtained from natural sources or chemically synthesized. The sensor proteins employed for this method include nuclear receptors, such as RXR, estrogen receptor, glucocorticoid receptor and the like, and intracellular binding proteins, such as cellular retinoic acid- and retinol-binding proteins, fatty acid binding proteins and the like. Protocols for screening ligands are similar to those described above except that different sensor proteins are used, as appropriate.

Although the invention has been described with respect to various embodiments, it should be realized this invention is also capable of a wide variety of further and other embodiments.

What is claimed is:

1. A method for measuring ligand concentration in a biological sample, comprising:
   (a) labeling a sensor protein;
   (b) generating a standard titration curve using said labeled sensor protein and ligand, wherein said labeled sensor protein is a mutant intracellular lipid-binding protein containing one cysteine residue, and wherein said ligand is selected from the group consisting of a retinoid, rexinoid, a fatty acid, and a natural or synthetic ligand that activates a nuclear receptor;
   (c) adding said labeled sensor protein to said biological sample;
   (d) allowing said ligand to bind to said sensor protein to produce a change in signal; and
   (e) measuring said concentration of said ligand in said biological sample by comparing said change in signal to said standard titration curve.

2. The method of claim 1, wherein said intracellular lipid-binding protein is selected from the group consisting of mutant cellular retinol binding proteins (CRBPs), mutant cellular retinoic acid binding proteins (CRABPs), and mutant fatty acid binding proteins (FABPs).

3. The method of claim 2, wherein said CRABPs is either mutant CRABP-I or mutant CRABP-H.

4. The method of claim 1, wherein said retinoid is selected from the group consisting of all-trans-retinoic acid, 4-oxo-retinoic acid, and 9-cis-retinoic acid.

5. The method of claim 1, wherein said natural or synthetic ligand that activates a nuclear hormone receptor is selected from the group consisting of fibrates, GW-501516, and thiazolidinediones.

6. The method of claim 1, wherein said label is selected from a fluorescent compound.

7. The method of claim 6, wherein said fluorescence label is bromomethyl fluorescein.

8. The method of claim 1, wherein said biological sample is a tissue or cell extract.

9. The method of claim 8, wherein said tissue extract is selected from the group consisting of kidney, liver, lung, eye, breast, muscle, and intestine.

10. The method of claim 1, wherein said biological sample is a biological fluid.

11. The method of claim 10, wherein said biological fluid is selected from the group consisting of sera, urine, aqueous humor, vitreous humor, bodily excretions, and blood.

* * * * *

UNITED STATES PATENT AND TRADEMARK OFFICE
CERTIFICATE OF CORRECTION

PATENT NO. : 7,759,069 B1
APPLICATION NO. : 11/294736
DATED : July 20, 2010
INVENTOR(S) : Noa Noy Page 1 of 1

It is certified that error appears in the above-identified patent and that said Letters Patent is hereby corrected as shown below:

In column 26, line 33 (claim 3), "CRABP-H" should read -- CRABP-II --

Signed and Sealed this

Thirty-first Day of August, 2010

David J. Kappos
*Director of the United States Patent and Trademark Office*